, 
United States Patent

Miyazaki et al.

[11] Patent Number: 5,916,619
[45] Date of Patent: Jun. 29, 1999

[54] FRIED INSTANT NOODLES AND METHOD FOR MANUFACTURING THE SAME

[75] Inventors: Eiji Miyazaki; Hajime Akashi; Miwa Takahashi, all of Saitama-ken; Yasuhiro Tanaka; Shoji Yokozuka, both of Tokyo, all of Japan

[73] Assignee: Nisshin Flour Milling Co., Ltd., Tokyo, Japan

[21] Appl. No.: 08/608,314

[22] Filed: Feb. 28, 1996

[30] Foreign Application Priority Data

Mar. 6, 1995 [JP] Japan .................................... 7-070485

[51] Int. Cl.⁶ ...................................................... A23L 1/162
[52] U.S. Cl. .............................. 426/557; 426/18; 426/28; 426/451; 426/555; 426/622
[58] Field of Search ................................ 426/18, 28, 557, 426/451, 555, 458, 622, 661, 498, 502–504, 506–511, 549

[56] References Cited

U.S. PATENT DOCUMENTS

| | | | |
|---|---|---|---|
| 3,930,029 | 12/1975 | Minami et al. | 426/18 |
| 4,234,612 | 11/1980 | Sakakibara et al. | 426/394 |
| 4,234,617 | 11/1980 | Sakakibara et al. | 426/557 |
| 4,320,151 | 3/1982 | Cole | 426/18 |
| 4,469,711 | 9/1984 | Seltzer | 426/557 |

FOREIGN PATENT DOCUMENTS

| | | |
|---|---|---|
| 62-130921 | 3/1989 | Japan . |
| 1-152857 | 4/1991 | Japan . |
| 5-30431 | 5/1993 | Japan . |
| 9201384 | 2/1992 | WIPO . |

OTHER PUBLICATIONS

Better Homes and Gardens Oriental Cook Book, pp. 80–81, 1977.
The Good Cook Pasta, pages, p. 65, 1980.

*Primary Examiner*—Lien Tran
*Attorney, Agent, or Firm*—Oblon, Spivak, McClelland, Maier & Neustadt, P.C.

[57] ABSTRACT

A method for manufacturing a fried instant noodle wherein noodle strings comprising cereal flours, a chemical leavening agent and at least one enzyme selected from the group consisting of amylase and protease are steamed and then fried. The fried instant noodles exhibit a low oil absorption, a low calorie content, no oily odor or flavor and superior gastronomical taste and texture. The noodles can be reconstituted to a ready to eat state in a short time.

11 Claims, No Drawings

FRIED INSTANT NOODLES AND METHOD FOR MANUFACTURING THE SAME

This invention relates to fried instant noodles, a method for manufacturing the same and a cereal flour mix composition suitable for the manufacture of the fried instant noodles.

BACKGROUND OF THE INVENTION

Instant noodles have a widespread consumer's support for their superior instant cooking characteristics by which the noodles can be very easily made ready to eat by merely pouring boiling water onto the noodles in a dish or heat-cooking in a short time, and for their characteristics as a staple food and their good preservative quality. Those instant noodles are classified according to the drying method into a fried noodle (fried type), a hot air-dried noodle (non-fried type) and a freeze-dried noodle (freeze-dried type). The fried type, in particular Chinese-style noodles are at the top of the instant noodles, since they are very good in respect of instant cooking, handling, ease of manufacture, keeping quality and the like, with a low price.

The fried instant noodles absorb a large amount of oil when fried in oil, which results in higher calorie than non-fried noodles and freeze-dried noodles. In recent years, there is a strong consumer demand for fried instant noodles with low oil absorption, since the consumer has become highly dedicated to reducing calories in order to prevent diseases of adult people and the like. In addition, there has been a tendency toward good, light gastronomical texture with no oiliness in the fried instant noodles. Therefore, fried instant noodles are desired with low oil absorption.

Japanese Patent Publication No. 30431/93 has proposed a method for manufacturing the instant noodles wherein raw noodle strings containing an alkaline gas generating base (an alkaline chemical leavening agent) are prepared, an aqueous acidic solution is applied to the raw noodle strings, the noodle strings are steamed, expanded and dried using a hot air, frying in oil or the like to give the final instant noodles. Further, it is mentioned therein that this method can reduce the oil content of the dried noodle even when dried in oil, thus providing improved keeping quality of the product. However, the problems remain that the resulting dried noodles have a nutritiously high calorie and some oiliness and oily odor still remain therein, as a result of satisfactorily reduced effect being not achieved by the prior method.

SUMMARY OF THE INVENTION

An object of the present invention is to provide fried instant noodles having much lower oil absorption, lower calories, much less oiliness and oily odor and good taste and texture, as compared with the prior fried instant noodles. Further, the present noodles can be reconstituted to a ready to eat state in a short time as the prior fried instant noodles can do.

Another object of the invention is to provide a method for manufacturing such fried instant noodles.

A further object of the invention is to provide a cereal flour mix composition suitable for the manufacture of the fried instant noodles having lower oil absorption, as outlined above.

To achieve these objects, the present inventors conducted many repeated studies of the details of cereal raw materials used in the manufacture of fried instant noodles, of types of additives, and of noodle manufacturing methods, frying methods and the like. As a result, it was found that when noodle strings containing a chemical leavening agent and at least one enzyme selected from the group consisting of amylase and protease are prepared, steamed and then fried, the resulting fried instant noodles are of greatly reduced oil absorption, extremely low calories, a very low oiliness and oily odor, and superior gastronomical texture and taste, in comparison with the case of the prior art using the chemical leavening agent alone. It was also found that the present fried instant noodles can be restored to a ready to eat state in a short time, as the prior fried instant noodles can do.

Thus, the present invention provides a method for manufacturing fried instant noodles wherein noodle strings containing a chemical leavening agent and at least one enzyme selected from the group consisting of amylase and protease are steamed and then fried.

The present invention also includes fried instant noodles manufactured by this method.

The present invention also provides a cereal flour mix composition for fried instant noodles which comprises cereal flours, a chemical leavening agent and at least one enzyme selected from the group consisting of amylase and protease.

DETAILED DESCRIPTION OF THE INVENTION

In the manufacture of the fried instant noodles, the present invention can employ process steps of steaming the noodle strings followed by frying, which have been usually employed for the fried instant noodles. However, the present invention further requires that the noodle strings should contain at least one enzyme selected from the group consisting of amylase and protease, together with a chemical leavening agent.

Any chemical leavening agent approved as a food additive can be used in the present invention, which undergoes a chemical reaction and/or decomposition at the heating temperature in the steaming process and/or the frying process of the noodle strings, in particular, at the heating temperature in the steaming process, thereby to produce carbon dioxide gas or other gas. Examples of chemical leavening agents which can be used in the invention include at least one gas generating agent such as sodium hydrogen carbonate, ammonium carbonate, ammonium dicarbonate, potassium carbonate, and the like; and a mixture of the above gas generating agents with one or more gas generating promotion agents such as tartaric acid, potassium hydrogen tartrate, fumaric acid, sodium fumarate, glucono delta-lactone, calcium primary phosphate, sodium phosphate, anhydrous ammonium aluminum chloride (burnt ammonium alum), anhydrous potassium aluminum sulfate (burnt alum), disodium dihydrogen pyrophosphate and the like. A combination of sodium hydrogen carbonate with glucono delta-lactone or burnt ammonium alum is preferably used from the aspects of volume of gas generated and taste.

For the purpose of manufacturing fried instant noodles with low oil absorption and superior gastronomical texture and taste, it is desirable to prepare the noodle strings by adding the chemical leavening agent in an amount of 0.5 to 5 parts by weight (this being the total amount when more than one chemical leavening agent are used together), more preferably 1 to 2 parts by weight based on 100 parts by weight of the cereal flours used to make the noodle strings. With less than 0.5 part by weight, no reduction of absorbed oil is obtained in the fried instant noodles. With more than 5 parts by weight, the amount of oil absorbed in the fried instant noodles is not greatly reduced, but a harsh taste or abnormal taste is produced from using the large amount of chemical leavening agents so that the taste of the fried instant cooking noodles deteriorates.

As outlined above, the present invention requires that the noodle strings must contain at least one enzyme selected from the group consisting of amylase and protease, in addition to the chemical leavening agent.

It is not evident why fried instant noodles with a very reduced amount of oil absorption can be produced by the present invention using at least one of the above enzymes together with a chemical leavening agent, in contrast with the prior art using the chemical leavening agent alone. This will be presumed as mentioned below.

When the steamed noodles are fried in oil, the moisture contained in the noodle string vaporizes suddenly and the noodle string expands excessively into a porous structure. Oil is incorporated in the voids of the porous structure, which results in instant noodles with a high oil content.

According to the present invention, however, the raw cereal flour is digested under the action of the enzyme in the preparation of the noodle dough, so that the dough is softened. When the noodle string obtained from the softened dough is steamed, the interior and the surface of the noodle string will expand more uniformly and minutely than the case of using the chemical leavening agent alone, thus forming into a moderate porous condition. When the moisture in the noodle string vaporizes off in the step of frying, the moderate porous structure having many passages for the vapor to escape can inhibit excessive expanding during the frying process. Thus, the volume of the voids in the noodle string will be reduced, so that the amount of oil incorporated in these voids is reduced, which can provide the reduced oil absorption as in the present invention.

The enzyme used in the present invention may be a pure material or any food material containing at least one of the above-mentioned enzymes. Examples of the food materials can include malt, wheat germ or the like.

To produce fried instant noodles with a low oil absorption and superior gastronomical texture and taste, the amount of enzyme used is preferably in the range of 0.05 to 100 U of enzyme activity (total activity for the combined use of the plural enzymes), more preferably, 0.1 to 50 U for 1 g of cereal flour used to make the noodle string. The activity (U) of the enzyme (amylase or protease) as defined here refers to the activity (U) measured by the method stated in the following examples.

Representative processes for manufacturing noodle strings can include the following:
(1) a method wherein raw materials for noodles are kneaded to make a dough, the dough is compounded and rolled into a sheet and this sheet is cut into noodle strings; and
(2) an extrusion method wherein raw materials for noodles are kneaded in the same manner as for pasta and the resulting dough is extruded into noodle strings using an extruder.

No limitation is made in the present invention on the method for producing the noodle strings which has not been subjected to steaming. Either the above method (1) or the above method (2) may be used. Depending on circumstances, the noodle strings may be produced by other methods than the above methods (1) and (2), e.g., a manual rolling method, a vacuum extrusion method or the like. No particular limitation is made in the present invention as to the processes and conditions for kneading; for compounding and rolling; for cutting the noodle strings; and for extruding the noodle strings or as to the type of equipment used for those processes. Those processes can be carried out in accordance with known processes depending on the type of noodle.

In the steaming process of the noodle strings, they are preferably in the raw state or half-dried to such a degree that the chemical leavening agent and enzyme contained in the noodle string do not lose their activity. This is desirable in that the subsequent steaming of the noodle strings can be performed smoothly and fried instant noodles with low oil absorption can be obtained.

So long as the chemical leavening agent and the enzyme are mixed uniformly in the noodle strings, no particular restriction is made in the present invention on the method of adding them. The noodle strings containing the chemical leavening agent and enzyme can be manufactured, for example, by [1] a method of adding the chemical leavening agent and enzyme to the cereal flours for the production of the noodles, optionally together with other ingredients, further adding water, kneading the mixture to form a dough and producing the noodle strings from the dough according to the above-mentioned method (1) or (2) or other methods; or by [2] a method of adding other ingredients, as required, to the cereal flours for the manufacture of the noodles, further adding the chemical leavening agent and the enzyme dissolved in water, kneading the mixture to form a dough, and producing the noodle strings from the dough according to the above-mentioned method (1) or (2) or other methods. In either case, it is desirable that the chemical leavening agent and enzyme are added prior to kneading the dough or at the start of the kneading step, since the chemical leavening agent and enzyme can be uniformly dispersed in the dough and the softening of the dough proceeds to produce fried instant noodles with low oil absorption.

A dry cereal flour mix composition obtained by adding the chemical leavening agent and enzyme to the cereal flours for the manufacture of the noodles and further adding other ingredients, as required, can be distributed and sold as a cereal flour mix composition for fried instant noodles.

Thus, the present invention also provides a cereal flour mix composition for fried instant noodles, which comprises cereal flours, a chemical leavening agent and at least one enzyme selected from the group consisting of amylase and protease, and optionally other components.

The thickness, width, diameter and the like of the noodle string can be adjusted depending on the type of fried instant noodles and the like. In general, a noodle string with the thickness of about 0.7 to 1.6 mm and the width of about 1.0 to 2.0 mm, or a noodle string with the diameter of about 0.9 to 1.5 mm is preferred in that the subsequent steaming and frying can be carried out smoothly and the resulting fried instant noodles can exhibit reduced oil absorption.

Any cereal flour conventionally used in the manufacture of noodles can be used, examples of which include wheat flour, durum wheat flour, rye flour, soybean flour, oat flour, buckwheat flour, rice flour; starches such as potato starch, tapioca starch, corn starch and the like; the alpha converted form of these cereal flours; dogtooth violet starch; yam starch and the like. These cereal flours may be used alone or in admixture therewith. The cereal flour may be selected depending on the variety of noodle to be manufactured.

In addition to cereal flours, chemical leavening agents and enzymes, one or more additives and raw materials as used hitherto may be used depending on the type of fried instant noodle. Examples of such additives and raw materials include "Kansui", salt, emulsifying agents, protein enhancing agents, polysaccharides for increasing viscosity, oligosaccharides, polymerized phosphates, coloring materials, nutrition enhancing agents, powdered chlorella, powdered skim milk, powdered vegetables, powdered seaweeds, antioxidants, whole egg, egg white and the like.

The noodle strings containing a chemical leavening agent and enzyme manufactured as described above are subjected to a steaming. The steam temperature is preferably in range of 95–100° C. When a noodle string is steamed in the above steam temperature range, only the surface of the noodle string is normally gelatinized. Upon steaming of the noodle strings, part or all of the leavening agent undergo a decomposition or a chemical reaction to generate gas, so that the noodle string expands and the surface and inside of the noodle string becomes a porous structure. In this case, the expanding of the noodle string is inadequate if the chemical leavening agent is used alone. In the present invention, at least one enzyme selected from the group consisting of amylase and protease is used together with a chemical leavening agent. Thus, the ability of trapping the gas is improved as a result of the softness of the noodle string (dough) caused by these enzymes, so that the expanding of the noodle string is more accelerated at the surface and inside thereof and a uniform porous structure is created. As a result, the drying of the expanded noodle string is performed more smoothly and swiftly in the subsequent frying process so that a fried instant noodle with a greatly reduced oil absorption is obtained.

There is no particular restriction on the steaming process for the noodle strings. Any process and apparatus conventionally used in the steaming of instant noodles can be employed. For example, the noodle strings are processed with steam at a temperature of 95° C. to 100° C. until the moisture content is reached to the extent of 28 to 35 wt %, while transferring continuously the noodle strings on a net conveyor or the like, or by packing the noodle strings in a basket or the like and placing in a batch-wise, steam chamber.

Subsequently, the steamed noodles are fried in the same manner as in manufacturing conventional fried instant noodles, while disentangling the steamed noodle strings. For example, each single serving or several servings are filled into a retainer, a frame or the like to provide one package noodle, and the one package noodle is fried and dehydrated to manufacture the fried instant noodles. In this case, the frying of the one package noodle may be performed using the same method and equipment as used for manufacturing conventional fried instant noodles. This frying process is not limited. Generally, edible oils such as palm oil, partially hydrogenated palm oil, pure lard, modified lard, and mixtures of these are used. The noodle strings are fried for about 1 to 3 minutes at temperatures of about 130–150° C.

The resulting fried noodles are cooled, packed, cartoned and encased in a conventional manner, and then can be stored, distributed and sold.

By carrying out the series of processes as outlined above, fried instant noodles of the present invention are obtained, having lower oil absorption, a lower calorie content, a lower oily odor or oiliness than the conventional product, and superior gastronomical taste and texture. The present noodles can also be restored to a ready to eat state in a short time.

The kind of fried instant noodles manufactured by the present invention is not limited, examples of which can include Chinese-style noodles; Japanese-style noodles such as instant udon and instant soba; and European-style noodles.

The fried instant noodles of the present invention may be flavored and seasoned, or alternatively accompanied by a packet of soup.

The present invention is further illustrated by the following non-limitative examples, in which % is by weight unless otherwise stated. In the following examples, the activities of amylase and protease are measured in the following manner.

Method of measuring activity of amylase (1) Preparation of substrate solution

Potato starch (pharmaceutical grade) was dried for two hours at 105° C. Precisely 1.000 g of this dried material was weighed out, 20 ml of water was added, and the mixture was thoroughly stirred using a stirrer, while 5 ml of a 1 N sodium hydroxide solution was added to make a paste. The paste-like material was heated for five minutes in a boiling water bath, then cooled by the addition of 25 ml of cold water. The pH was then adjusted to 7.0±0.1 with a 1 N phosphoric acid solution. Twenty ml of a 0.5 M phosphate buffer solution (pH 7.0) was then added, and the mixture was diluted to 100 ml with distilled water to complete the preparation of the substrate solution.

(2) Preparation of 1/5000 N iodine solution

Fifty grams of potassium iodide was dissolved in 100 ml of distilled water, then 12.69 g of iodine were added and completely dissolved, after which more distilled water was added to give a total volume of 1000 ml, completing the preparation of a 0.1 N iodine solution. This solution was stored in a brown bottle. Prior to use, a 1/5000 N iodine solution was prepared as follows. One ml of 0.1 N iodine solution was mixed with 10 ml of a 1 N hydrochloric acid solution and diluted to 500 ml with distilled water.

(3) Measurement of absorbance (i) Ten ml aliquots of the substrate solution prepared as under (1) above were incubated in a water bath at 40+0.1° C. for 10 to 15 minutes. One ml of enzyme solution was then added, the test tube was stoppered and shaken vigorously to thoroughly mix the contents, and immediately held at 40±0.1° C. At exactly 10 min after the addition of the enzyme solution, one ml of this solution was measured out into 10 ml of 0.1 N hydrochloric acid solution which had previously been placed in a test tube (18 mm diameter, 180 mm length) equipped with a stopper. The test tube was then stoppered and well shaken. One ml of this liquid was added to 10 ml of the 1/5000 N iodine solution prepared under (2) above which had previously been placed in a test tube (18 mm diameter, 180 mm length) equipped with a stopper. This test tube was then stoppered and well shaken. The solution was then placed in a cell with a 10 mm optical path length and its absorbance ($A_1$) was measured at a wave length of 660 nm, with distilled water as a control.

(ii) Using one ml of distilled water as a blank, in place of the enzyme solution, the absorbance ($A_0$) was measured in the same manner as outlined in (i) above.

(4) Preparation of enzyme solution

Enzyme solutions were prepared by measuring out predetermined amounts of enzyme (amylase) used in the following examples and comparative examples, and dissolving these predetermined amounts in any suitable dilution liquid such as 50 mM tris-hydrochloric acid buffer solution (7.2 pH). The dilution ratio is such that $(A_0-A_1)/A_0$ which is the decomposition ratio of each enzyme (amylase) is 0.2 to 0.4.

(5) Calculation of enzyme activity

One Unit (U) is the amount of enzyme which reduces the blue iodine coloring in starch by 1% in one minute under the above-mentioned conditions. Accordingly, the enzyme (amylase) activity (U)(Unit) is given by the following numerical formula.

$$\text{Amylase activity } (U/g) = \{(A_0 - A_1)/A_0\} \times 100 \times 1/10 \times n$$
$$= \{(A_0 - A_1)/A_0\} \times 10 \times n$$

where
- $A_0$=absorbance of the blank
- $A_1$=absorbance of the enzyme decomposed substrate
- n=dilution ratio of the enzyme Method of measuring activity of protease (1) Preparation of substrate solution (milk casein solution)

1.5 g of milk casein ("Hamersteine" manufactured by Merck) were weighed out, 25 ml of 0.1 N sodium hydroxide solution were added, and the mixture was held for 10 min in a hot water bath at 90–95° C. to dissolve, then the solution was cooled with cold water. After cooling, 0.1 N phosphoric acid was added to adjust the pH to 7.0. In addition, 20 ml of 0.1 M phosphoric acid buffer solution adjusted to a pH of 7 and cold water were added to give 100 ml of the prepared milk casein solution.

(2) Preparation of reaction stop solution 1000 ml of 0.4 M trichloroacetic acid solution were prepared by dissolving 65.36 g of trichloroacetic acid in water. This solution was used as a reaction stop solution.

(3) Preparation of enzyme solution (protease test solution)

Enzyme solutions were prepared by dissolving 0.5 g of the enzyme (protease) used in the examples and comparative examples in 150 ml of any suitable dilution solution such as 50 mM tris-hydrochloric acid buffer solution (7.2 pH). One ml of this solution was then measured out and made up to 100 ml using the same dilution liquid (30,000 times dilution) to give the enzyme solution.

(4) Measurement of absorbance (i) One ml of the substrate solution (milk casein solution) prepared under (1) above was measured into a test tube (15 mm diameter, 150 mm length), placed in a constant temperature water bath at 37±0.5° C., and preheated for 5 min. Exactly 1 ml of the enzyme solution (protease test solution) prepared under (3) above was added and well shaken, the test tube was placed in the constant temperature water bath at 37±0.5° C. and held for 60 min. Two ml of the reaction stop solution prepared under (2) above were added and well shaken, the test tube was placed in the constant temperature water bath at 37±0.5° C. and held for 25 min. The solution was then filtered using a No. 131 filter paper (7 cm diameter). One ml of the filtrate was measured into a test tube (18 mm diameter, 180 mm length), after which 5 ml of 0.4 M sodium carbonate solution and 1.0 ml of Folin-Ciocalteau's reagent ("Phenol reagent" manufactured by Wako Junyaku Kogyo, K. K.) diluted five times with distilled water were added. The mixture was thoroughly shaken to mix, then placed in the constant temperature water bath at 37±0.5° C. and held for 20 min for color to develop. After the color had developed, the absorbance ($A_t$) was measured at a wave length of 660 nm, with distilled water as a control.

(ii) Separately, as a blank test, one ml of the substrate solution (milk casein solution) prepared under (1) above was measured into a test tube (15 mm diameter, 150 mm length), 2 ml of 0.4 M trichloroacetic acid solution were added, and the mixture was thoroughly shaken to mix. Exactly 1 ml of distilled water was added and well shaken, the test tube was immediately placed in the constant temperature water bath at 37±0.5° C. and held for 60 min. Two ml of the reaction stop solution prepared under (2) above were then added and well shaken, the test tube was placed in the constant temperature water bath at 37±0.5° C. and held for 25 min. The solution was then filtered using a No. 131 filter paper (7 cm diameter). One ml of the filtrate was measured into a test tube (18 mm diameter, 180 mm length), after which 5 ml of 0.4 M sodium carbonate solution and 1.0 ml of Folin-Ciocalteau's reagent ("Phenol reagent" manufactured by Wako Junyaku Kogyo, K.K.) diluted five times with distilled water were added. The mixture was thoroughly shaken to mix, then placed in the constant temperature water bath at 37±0.5° C. and held for 20 min for color to develop. After the color had developed, the absorbance ($A_0$) was measured at a wave length of 660 nm, with distilled water as a control.

(iii) Preparation of tyrosine calibration curve

Standard tyrosine was dried for 3 hours at 105° C., then 0.100 g were accurately weighed out and dissolved in 0.1 N hydrochloric acid solution to give a volume of exactly 100 ml. Volumes of exactly 1 ml, 2 ml, 3 ml, 4 ml and 5 ml of this solution were measured out, and 0.1 N hydrochloric acid solution was added to each of these portions to bring the volume up to exactly 100 ml. One ml of these solutions then contained 10 µg, 20 µg, 30 µg, 40 µg, and 50 µg respectively of tyrosine. Subsequently, one ml of each of these solutions was accurately measured out, then 5 ml of 0.4 M sodium carbonate solution and 1.0 ml of Folin-Ciocalteau's reagent ("Phenol reagent" manufactured by Wako Junyaku Kogyo, K.K.) diluted five times with distilled water were added to each. The mixtures were thoroughly shaken to mix, then placed in the constant temperature water bath at 37±0.5° C. and held for 20 min for color to develop. After the color had developed, the absorbances $A_1$, $A_2$, $A_3$, $A_4$, and $A_5$ were measured at a wave length of 660 nm, with distilled water as a control. Separately, the absorbance $A_0$ was measured for a solution made up by the same method using 1 ml of 0.1 N hydrochloric acid solution in place of the tyrosine standard solution. From these results, a calibration curve was prepared by plotting the weight of tyrosine (µg) contained in one ml of these various solutions as abscissa and the absorbance differences [$A_1-A_0$, $A_2-A_0$, $A_3-A_0$, $A_4-A_0$, and $A_5-A_0$] as ordinate. The tyrosine (F µg) corresponding to an absorbance difference of 1.000 was thus obtained.

(5) Calculation of protease activity

One Unit (1 U) of protease strength is defined as the amount of enzyme which produces amino acid corresponding to 100 µg of tyrosine in 1 ml of the reaction filtrate for 60 min. The protease activity is calculated by the following numerical formula.

$$\text{Protease activity } (U/g) = \{(A_t - A_0) \times F \times 1/100 \times n$$

where
- $A_0$=absorbance of the blank
- $A_t$=absorbance of the enzyme decomposed substrate
- F=amount of tyrosine (µg) when the absorbance difference is 1.000, obtained from the tyrosine calibration curve
- n=dilution ratio of the test solution

EXAMPLE 1

(1) 1.0 part by weight of a chemical leavening agent with the composition shown in the following Table 1 (powder type synthetic chemical leavening agent manufactured by Oriental Yeast Co., Ltd.) and the amount of amylase (Amylase AD "Amano" manufactured by Amano Pharmaceutical Co., Ltd.) shown in the following Table 3 were added to 100 parts by weight of hard wheat flour ("TOKU NUMBER ONE" manufactured by Nisshin Flour Milling Co., Ltd.). In addition, 29 parts by weight of an aqueous solution of one part by weight of salt and 0.2 parts by weight of "Kansui" in 27.8 parts by weight of water were added to the above and the mixture was kneaded for 10 min by a conventional method to produce a dough. Then, this dough was rolled by a conventional method using noodle-making rolls to give a sheet of 1.0 mm thickness. The sheet was then cut into noodle strings using a pair of No. 20 cutting rolls.

(2) The respective noodle strings obtained in (1) above were placed in steaming baskets and steamed for 3 min at a steam temperature of 100° C., discharged from the steaming basket, and fried for 80 sec in refined palm oil at 135° C. to 140° C., to manufacture various Chinese fried instant noodles.

TABLE 1

| Chemical leavening agent composition | |
| --- | --- |
| Potassium aluminum sulfate | 8.8 wt % |
| Calcium dihydrogen phosphate | 8.9 wt % |
| Calcium hydrogen phosphate | 1.1 wt % |
| Fumaric acid | 2.7 wt % |
| Disodium dihydrogen pyrophosphate | 13.2 wt % |
| Glucono delta-lactone | 16.0 wt % |
| Sodium hydrogen carbonate | 40.0 wt % |
| Starch | 9.3 wt % |
| Total | 100.0 wt % |

(3) Using part of the steamed noodles and the fried Chinese instant noodles obtained in (2) above, the oil absorption ratio and oil absorption reduction ratio of the Chinese fried instant noodles were measured in the following manner. The results are shown in Table 3.

Oil absorption ratio of fried instant noodles
(i) The fried instant noodles were allowed to cool and the weight (W) (g) was measured.
(ii) The cooled fried instant noodles were dried for 2 hr at 135° C. to determine the moisture content ($M_1$) (%). Using this value of the moisture content, the dry weight (Wi) (g) of the fried instant noodles for which the weight (W) had been measured in (i) above was calculated.
(iii) The weight (Wii) (g) of the steamed noodles obtained under (2) above was measured after cooling but prior to frying. The moisture was removed by drying for one hour at 135° C. and the moisture content ($M_2$) (%) was determined. Using this value of the moisture content, the dry weight (Ws) (g) of the steamed noodles corresponding to the fried instant noodles for which the weight (W) had been measured in (i) above was obtained by the numerical formula given below.
(iv) From the weight (W) (g) of the fried instant noodles, the dry weight (Wi) (g) of the fried instant noodles and the dry weight (Ws) (g) of the steamed noodles obtained as above, the oil absorption ratio of the fried instant noodles was calculated using the following formulae.

Dry weight of fried instant noodles $(Wi)$ $(g) = W \times \{1-(M_1/100)\}$

Dry weight of steamed noodles $(Ws)$ $(g) = Wii \times \{1-(M_2/100)\}$

Oil absorption ratio (%) of fried instant noodles $= \{(Wi-Ws)/W\} \times 100$

Oil absorption reduction ratio
With the oil absorption ratio of fried instant noodles obtained from noodle strings which contain neither a chemical leavening agent nor an enzyme (the fried instant noodles of Test No. 1 of Example 1 and Test No. 11 of Example 2) as the criterion, the oil absorption reduction ratio of the fried instant noodles obtained from Test Nos. 2 to 10 of Example 1, Test Nos. 12 to 20 of Example 2, and Examples 3 to 9 were obtained using the following numerical formula.

Oil absorption reduction ratio $(\%) = \{(A-B/A)\} \times 100$ wherein
A = oil absorption ratio (%) of fried instant noodles obtained form noodle strings which contain neither a chemical leavening agent nor an enzyme
B = oil absorption ratio (%) of fried instant noodles obtained from noodle strings containing one or both of a chemical leavening agent and an enzyme (4) Furthermore, 100 g of each of the respective Chinese fried instant noodles obtained in (2) above were reconstituted by immersion for 3 min in 600 ml boiling water. These reconstituted noodles were subjected to organoleptic testing by a panel of 10 members according to the evaluation criteria shown in the following Table 2. The average values of these organoleptic tests are given in Table 3. The organoleptic tests were also conducted on the Chinese fried instant noodles of Test No. 1 of Example 1 and Test No. 11 of Example 2, produced using noodle strings containing neither a chemical leavening agent nor an enzyme, as a control (three-point as a standard).

TABLE 2

Criteria for organoleptic evaluation of fried instant noodles
Degree of elasticity
5: Very good, good degree of elasticity, as compared with control
4: Good, proper degree of elasticity, as compared with control
3: Same degree of elasticity as control
2: Slightly inferior degree of elasticity, slightly soft or slightly hard, as compared with control
1: Poor degree of elasticity, extremely soft or extremely hard, as compared with control
Degree of smoothness
5: Very good; very superior smoothness, as compared with control
4: Good; superior smoothness, as compared with control
3: Same degree of smoothness as control
2: Poor; inferior degree of smoothness, as compared with control
1: Very poor; smoothness much less than control
Oily odor, oiliness and taste
5: Good taste; oily odor and oiliness much reduced, as compared with control
4: Fairly good taste; oily odor and oiliness slightly reduced, as compared with control
3: Oily odor, oiliness and taste same as control
2: Slightly inferior taste; oily odor and oiliness slightly increased, as compared with control
1: Poor taste; oily odor and oiliness much increased, as compared with control

TABLE 3

| Test No. | Ratio of Chemical leavening agent added[1] (%) | Ratio of enzyme added[2] (%) | Oil absorption ratio (%) | Oil absorption reduction ratio (%) | Organoleptic tests for fried instant noodles | | |
|---|---|---|---|---|---|---|---|
| | | | | | Degree of elasticity | Smoothness | Oily odor, oiliness and taste |
| 1 | 0 | 0 (0 U) | 21.0 | 0.0 | 3.0 | 3.0 | 3.0 |
| 2 | 2 | 0 (0 U) | 19.3 | 8.1 | 3.0 | 3.0 | 3.0 |
| 3 | 2 | $5 \times 10^{-4}$ (0.05 U) | 18.3 | 12.9 | 3.0 | 3.2 | 3.4 |
| 4 | 2 | $1 \times 10^{-3}$ (0.10 U) | 17.8 | 15.2 | 3.0 | 3.2 | 4.0 |
| 5 | 2 | $1 \times 10^{-2}$ (1 U) | 17.2 | 18.1 | 3.0 | 3.4 | 4.0 |
| 6 | 2 | $1 \times 10^{-1}$ (10 U) | 16.6 | 21.0 | 3.0 | 3.5 | 4.3 |
| 7 | 2 | $2 \times 10^{-1}$ (20 U) | 15.5 | 26.2 | 3.0 | 3.4 | 4.4 |
| 8 | 2 | $5 \times 10^{-1}$ (50 U) | 14.7 | 30.0 | 3.0 | 3.4 | 4.1 |
| 9 | 2 | 1 (100 U) | 14.3 | 31.9 | 3.0 | 3.4 | 3.6 |
| 10 | 2 | 2 (200 U) | 15.0 | 28.6 | 2.2 | 3.4 | 3.4 |

[1]Ratio of the chemical leavening agent added (wt %) based on weight of wheat flour
[2]Ratio of the enzyme added (wt %) based on weight of wheat flour (Figures in brackets indicate enzyme activity (U) added to 1 g of wheat flour.)

As can be seen from the results shown in Table 3, in the cases of the fried instant noodles of Test No. 1 obtained using noodle strings containing neither amylase nor a chemical leavening agent and the fried instant noodles of Test No. 2 obtained using noodle strings containing a chemical leavening agent but not amylase, the oil absorption ratio is larger and the calorie content is higher, an oily odor and oiliness are present, and the taste is inferior, in comparison with the fried instant noodles obtained from Test Nos. 3 to 10 obtained using noodle strings containing both a chemical leavening agent and amylase.

In addition, the results shown in Table 3 show that it is desirable that the amount of enzyme (amylase) contained in the noodle strings be 0.05 to 100 U, and more preferably be 0.1 to 50 U, for one gram of wheat flour used in the noodle strings.

EXAMPLE 2

(1) With the exception of 0.2 parts by weight of the same amylase used in Example 1 (amylase activity=20 U for 1 g of wheat flour) and the same amounts as shown in Table 4 of the chemical leavening agent used in Example 1 being added to 100 parts by weight of the same wheat flour used in Example 1, the respective fried instant noodles were manufactured in exactly the same manner as in Example 1.

The oil absorption ratio of the resulting fried instant noodles was obtained in the same manner as in Example 1, and 100 g of the resulting Chinese fried instant noodles were immersed in 600 ml of boiling water for 3 min to reconstitute the noodles. These noodles were subjected to the same organoleptic evaluation as in Example 1. The results are shown in Table 4.

TABLE 4

| Test No. | Ratio of Chemical leavening agent added[1] (%) | Ratio of enzyme added[2] (%) | Oil absorption ratio (%) | Oil absorption reduction ratio (%) | Organoleptic tests for fried instant noodles | | |
|---|---|---|---|---|---|---|---|
| | | | | | Degree of elasticity | Smoothness | Oily odor, oiliness and taste |
| 11 | 0 | 0 (0 U) | 21.0 | 0.0 | 3.0 | 3.0 | 3.0 |
| 12 | 0 | 0.2 (20 U) | 19.5 | 7.1 | 3.0 | 3.1 | 3.0 |
| 13 | 0.4 | 0.2 (20 U) | 18.9 | 10.0 | 3.0 | 3.1 | 3.1 |
| 14 | 0.5 | 0.2 (20 U) | 17.8 | 15.2 | 3.0 | 3.2 | 3.3 |
| 15 | 1 | 0.2 (20 U) | 16.4 | 21.9 | 3.0 | 3.4 | 4.4 |
| 16 | 2 | 0.2 (20 U) | 15.5 | 26.2 | 3.0 | 3.4 | 4.4 |
| 17 | 3 | 0.2 (20 U) | 15.7 | 25.2 | 3.0 | 3.4 | 3.4 |
| 18 | 5 | 0.2 (20 U) | 15.6 | 25.7 | 3.0 | 3.1 | 3.2 |
| 19 | 6 | 0.2 (20 U) | 15.8 | 24.8 | 2.9 | 3.0 | 2.8 |
| 20 | 10 | 0.2 (20 U) | 16.8 | 20.0 | 2.0 | 2.4 | 2.0 |

[1]Ratio of the chemical leavening agent added (wt %) based on weight of wheat flour
[2]Ratio of the enzyme added (wt %) based on weight of wheat flour (Figures in brackets indicate enzyme activity (U) added to 1 g of wheat flour.)

As can be seen from the results shown in Table 4, in the cases of the fried instant noodles of Test No. 11 obtained using noodle strings containing neither amylase nor a chemical leavening agent and the fried instant noodles of Test No. 12 obtained using noodle strings containing amylase but not a chemical leavening agent, the oil absorption ratio is larger and the calorie content is higher, an oily odor and oiliness are present, and the taste is inferior, in comparison with the fried instant noodles obtained from Test Nos. 13 to 20 obtained using noodle strings containing both a chemical leavening agent and amylase.

In addition, the results shown in Table 4 show that it is desirable that the amount of the chemical leavening agent contained in the noodle strings be 0.5 to 5 wt % (0.5 to 5 parts by weight of the chemical leavening agent to 100 parts by weight of wheat flour) and more preferably be 1 to 2 wt %, based on the amount of wheat flour used in the noodle strings.

EXAMPLE 3

With the exception of the addition of one part by weight of another amylase ("Takadiastase" manufactured by Sankyo Co., Ltd.) (amylase activity=50 U for 1 g of wheat flour) instead of the amylase AD "Amano", and one part by weight of the same chemical leavening agent used in Example 1, and the addition of 30 parts by weight of an aqueous solution of 0.2 parts by weight of "Kansui" and one part by weight of salt in 28.8 parts by weight of water to 100 parts by weight of the same wheat flour used in Example 1, the fried instant noodles were manufactured in exactly the same manner as in Example 1.

The oil absorption ratio of the resulting fried instant noodles was obtained in the same manner as in Example 1, and 100 g of the resulting Chinese fried instant noodles were immersed in 600 ml of boiling water for 3 min to reconstitute the noodles. These noodles were subjected to the same organoleptic evaluation as in Example 1. The results are shown in Table 5.

EXAMPLE 4

With the exception of the addition of 0.05 part by weight of another amylase (Ekikakouso T manufactured by Hankyu Bio Industry Co., Ltd.) (amylase activity=5 U for 1 g of wheat flour) instead of the amylase AD "Amano", and one part by weight of the same chemical leavening agent used in Example 1, to 100 parts by weight of the same wheat flour used in Example 1, the fried instant noodles were manufactured in exactly the same manner as in Example 1.

The oil absorption ratio of the resulting fried instant noodles was obtained in the same manner as in Example 1, and 100 g of the resulting Chinese fried instant noodles were immersed in 600 ml of boiling water for 3 min to reconstitute the noodles. These noodles were subjected to the same organoleptic evaluation as in Example 1. The results are shown in Table 5.

EXAMPLE 5

With the exception of the addition of 0.2 part by weight of another amylase ("Sumichyme L" manufactured by Shin Nippon Chemical Industry Co., Ltd.) (amylase activity=24 U for 1 g of wheat flour) instead of the amylase AD "Amano", and one part by weight of the same chemical leavening agent used in Example 1, to 100 parts by weight of the same wheat flour used in Example 1, the fried instant noodles were manufactured in exactly the same manner as in Example 1.

The oil absorption ratio of the resulting fried instant noodles was obtained in the same manner as in Example 1, and 100 g of the resulting Chinese fried instant noodles were immersed in 600 ml of boiling water for 3 min to reconstitute the noodles. These noodles were subjected to the same organoleptic evaluation as in Example 1. The results are shown in Table 5.

EXAMPLE 6

With the exception of the addition of 0.02 parts by weight of protease (Protease M "Amano" manufactured by Amano Pharmaceutical Co., Ltd.) (protease activity=1 U for 1 g of wheat flour) instead of amylase, and one part by weight of the same chemical leavening agent used in Example 1, to 100 parts by weight of the same wheat flour used in Example 1, the fried instant noodles were manufactured in exactly the same manner as in Example 1.

The oil absorption ratio of the resulting fried instant noodles was obtained in the same manner as in Example 1, and 100 g of the resulting Chinese fried instant noodles were immersed in 600 ml of boiling water for 3 min to reconstitute the noodles. These noodles were subjected to the same organoleptic evaluation as in Example 1. The results are shown in Table 5.

EXAMPLE 7

With the exception of the addition of 0.18 parts by weight of protease (Protease M "Amano" manufactured by Amano Pharmaceutical Co., Ltd.) (protease activity=10 U for 1 g of wheat flour), the fried instant noodles were manufactured in exactly the same manner as in Example 6.

The oil absorption ratio of the resulting fried instant noodles was obtained in the same manner as in Example 1, and 100 g of the resulting Chinese fried instant noodles were immersed in 600 ml of boiling water for 3 min to reconstitute the noodles. These noodles were subjected to the same organoleptic evaluation as in Example 1. The results are shown in Table 5.

EXAMPLE 8

With the exception of the addition of 0.1 part by weight of protease (Protease A "Amano" manufactured by Amano Pharmaceutical Co., Ltd.) (protease activity=10 U for 1 g of wheat flour) instead of amylase, and one part by weight of the same chemical leavening agent used in Example 1, to 100 parts by weight of the same wheat flour used in Example 1, the fried instant noodles were manufactured in exactly the same manner as in Example 1.

The oil absorption ratio of the resulting fried instant noodles was obtained in the same manner as in Example 1, and 100 g of the resulting Chinese fried instant noodles were immersed in 600 ml of boiling water for 3 min to reconstitute the noodles. These noodles were subjected to the same organoleptic evaluation as in Example 1. The results are shown in Table 5.

EXAMPLE 9

With the exception of the addition of 0.01 part by weight of protease (Protease N "Amano" manufactured by Amano Pharmaceutical Co., Ltd.) (protease activity=15 U for 1 g of wheat flour) instead of amylase, and one part by weight of the same chemical leavening agent used in Example 1, to 100 parts by weight of the same wheat flour used in Example 1, the fried instant noodles were manufactured in exactly the same manner as in Example 1.

The oil absorption ratio of the resulting fried instant noodles was obtained in the same manner as in Example 1, and 100 g of the resulting Chinese fried instant noodles were immersed in 600 ml of boiling water for 3 min to reconstitute the noodles. These noodles were subjected to the same organoleptic evaluation as in Example 1. The results are shown in Table 5.

TABLE 5

| Example No. | Ratio of chemical leavening agent added[1] (%) | Enzyme Type | % Added[2] | Oil absorption ratio (%) | Oil absorption reduction ratio (%) | Organoleptic tests for fried instant noodles | | |
|---|---|---|---|---|---|---|---|---|
| | | | | | | Degree of elasticity | Smoothness | Oily odor, oiliness and taste |
| 3 | 1 | Takadiastase | 1 (50 U) | 15.7 | 25.2 | 3.2 | 3.2 | 4.5 |
| 4 | 1 | Ekikakouso T | 0.05 (5 U) | 17.4 | 17.1 | 3.0 | 3.3 | 4.0 |
| 5 | 1 | Sumichyme L | 0.2 (24 U) | 15.5 | 26.2 | 3.3 | 3.3 | 4.5 |
| 6 | 1 | Protease M "Amano" | 0.02 (1 U) | 16.9 | 19.5 | 3.1 | 3.2 | 4.1 |
| 7 | 1 | Protease M "Amano" | 0.18 (10 U) | 16.1 | 23.3 | 3.0 | 3.3 | 4.5 |
| 8 | 1 | Protease A "Amano" | 1.0 (10 U) | 16.8 | 20.0 | 3.0 | 3.2 | 4.1 |
| 9 | 1 | Protease N "Amano" | 0.01 (15 U) | 17.2 | 18.1 | 3.0 | 3.2 | 4.1 |

[1]Ratio of the chemical leavening agent added (wt %) based on weight of wheat flour
[2]Ratio of each enzyme added (wt %) based on weight of wheat flour (Figures in brackets indicate enzyme activity (U) added to 1 g of wheat flour.)

As can be seen from the results shown in Table 5, in all of the fried instant cooking noodles of Examples 3 to 9 obtained by steaming and frying the noodle strings containing either amylase or protease and a chemical leavening agent, the oil absorption ratio is small and the calorie content is low, there is no oily odor or oiliness present, and the gastronomical taste and texture are superior.

The fried instant noodles of the present invention exhibit an extremely low oil absorption when fried, which results in a low calorie content and preveting too much fats and oils from being taken up. In addition, there is very little oily odor or taste and the gastronomical flavor and texture are superior. Furthermore, the noodles can be reconstituted to a ready to eat state in a short time and the reconstituted noodles exhibit a superior smoothness and gastronomical texture.

What is claimed is:

1. A method for manufacturing a fried instant noodle wherein noodle strings comprising cereal flours, a chemical leavening agent and at least one enzyme selected from the group consisting of amylase and protease are steamed and then fried, wherein the chemical leavening agent is added in the amount of 0.5 to 5 parts by weight based on 100 parts by weight of cereal flour, and the activity of the enzyme is 0.05 to 100 U for each gram of the cereal flour used in manufacturing the noodle strings.

2. The method of claim 1, wherein the chemical leavening agent is added in the amount of 1 to 2 parts by weight based on 100 parts by weight of cereal flour.

3. The method of claim 1, wherein said at least one enzyme is amylase.

4. The method of claim 1, wherein said at least one enzyme is protease.

5. The method of claim 1, wherein the activity of the enzyme is 0.1 to 50 U for each gram of the cereal flours used in manufacturing the noodle strings.

6. A fried instant noodle manufactured by a method set forth in claim 1.

7. A cereal flour mix composition for fried instant noodles which consists essentially of cereal flours, a chemical leavening agent, and at least one enzyme selected from the group consisting of amylase and protease, wherein the chemical leavening agent is added in the amount of 0.5 to 5 parts by weight based on 100 parts by weight of the cereal flours, and 0.05 to 100 U of the enzyme are added per 1 g of the cereal flours.

8. The cereal flour mix composition of claim 7, wherein the chemical leavening agent is added in the amount of 1 to 2 parts by weight based on 100 parts by weight of the cereal flours.

9. The cereal flour mix composition of claim 7, wherein said at least one enzyme is amylase.

10. The cereal flour mix composition of claim 7, wherein said at least one enzyme is protease.

11. The cereal flour mix composition of claim 7, wherein 0.1 to 50 U of the enzyme are added per 1 g of the cereal flours.

* * * * *